(12) United States Patent
Earle et al.

(10) Patent No.: US 7,009,077 B2
(45) Date of Patent: Mar. 7, 2006

(54) AROMATIC SULFONATION REACTIONS

(75) Inventors: Martyn John Earle, Belfast (GB); Suhas Prabhakar Katdare, Belfast (GB)

(73) Assignee: The Queen's University of Belfast, Belfast (GB)

( * ) Notice: Subject to any disclaimer, the term of this patent is extended or adjusted under 35 U.S.C. 154(b) by 270 days.

(21) Appl. No.: 10/398,531

(22) PCT Filed: Oct. 5, 2001

(86) PCT No.: PCT/GB01/04427

§ 371 (c)(1), (2), (4) Date: Jun. 16, 2003

(87) PCT Pub. No.: WO02/30878

PCT Pub. Date: Apr. 18, 2002

(65) Prior Publication Data

US 2004/0242932 A1  Dec. 2, 2004

(30) Foreign Application Priority Data

Oct. 10, 2000 (GB) .................................. 0024747

(51) Int. Cl.
| | |
|---|---|
| C07C 303/00 | (2006.01) |
| C07C 307/00 | (2006.01) |
| C07C 309/00 | (2006.01) |
| C07C 311/00 | (2006.01) |
| C07C 313/00 | (2006.01) |

(52) U.S. Cl. ...................................................... 564/86
(58) Field of Classification Search ................... 564/86
See application file for complete search history.

(56) References Cited

U.S. PATENT DOCUMENTS

| | | | | | |
|---|---|---|---|---|---|
| 2,161,173 | A | * | 6/1939 | Kyrides ........................ | 562/93 |
| 2,267,725 | A | * | 12/1941 | Flett ............................ | 562/93 |
| 2,723,990 | A | * | 11/1955 | Gilbert et al. ................ | 562/95 |
| 2,813,917 | A | * | 11/1957 | Sharrah ....................... | 585/323 |
| 4,360,514 | A | * | 11/1982 | Buck ............................ | 424/56 |
| 6,348,631 | B1 | * | 2/2002 | Desmurs et al. ............ | 568/319 |

FOREIGN PATENT DOCUMENTS

| | | |
|---|---|---|
| DE | 98 030 C | 6/1898 |
| DE | 137 935 C | 12/1902 |

OTHER PUBLICATIONS

W. V. Farrar, "Reactions of some arenesulphonyl chlorides," *J. Chem. Soc.*, No. 7, Jul. 1960, pp. 3063-3069.
C. J. Adams et al., "Friedel-Crafts reactions in room temperature ionic liquids," *Chem. Commun.*, No. 19, Oct. 1998, pp. 2097-2098.

* cited by examiner

*Primary Examiner*—Johann Richter
*Assistant Examiner*—Chukwuma Nwaonicha
(74) *Attorney, Agent, or Firm*—Drinker Biddle & Reath LLP

(57) ABSTRACT

A process for the sulfonation of an aromatic compound wherein the aromatic compound and sulfonating agent are admixed in the presence of an ionic liquid is described. The method for the sulfonation of aromatic compounds in (e.g. water stable) ionic liquids offers advantages over conventional sulfonation reactions. These are that no by-products form, the ionic liquid is not consumed, and the sulfonating agent (e.g. $SO_3$) is relatively inexpensive.

19 Claims, No Drawings

AROMATIC SULFONATION REACTIONS

The present invention relates to a process for the sulfonation of aromatic compounds.

The sulfonation of aromatic compounds can be achieved by a number of methods. Classically this involves the reaction of an aromatic compound with oleum,[1] the reaction with sulfur trioxide in various organic solvents,[2] and reaction with sulfuric acid.[3] Fuming sulfuric acid, chlorosulfonic acid, the dioxane adduct of $SO_3$, amine adducts of $SO_3$,[4] are chiefly used as agents for sulfonating aromatic compounds by introducing a sulfonic acid group into the aromatic ring of the compound. However, the use of such agents for sulfonation involves various problems. For example, sulfuric acid or fuming sulfuric acid, when used, produce water as a by-product to result in a reduced conversion. To obtain high conversions, an excess of the sulfonating agent needs to be used, consequently producing a large amount of waste acid. On the other hand, use of chlorosulfonic acid produces waste hydrochloric acid. The adducts of $SO_3$ with dioxane or an amine with $SO_3$ are less reactive sulfonating agents, and although the adduct produces little waste acid, they cause problems with amine salt/dioxane disposal.

According to one aspect of present invention, there is provided a process for the sulfonation of an aromatic compound wherein the aromatic compound and sulfonating agent are admixed in the presence of an ionic liquid.

The method for the sulfonation of aromatic compounds in (e.g. water stable) ionic liquids offers advantages over conventional sulfonation reactions. These are that no by-products formed, the ionic liquid is not consumed and the sulfonating agent (e.g. $SO_3$ or $ClSO_3H$) is relatively inexpensive.

Room temperature ionic liquids have been used to great effect as solvents for a number of reactions,[5] for example Friedel-Crafts reactions,[6] isomerisations of fatty acid derivatives,[7] dimerisation reactions of alkenes,[8] Diels-Alder reactions[9] and hydrogenation reactions.[10]

Ionic liquids consist of two components, which are a positively charged cation and a negatively charged anion. Generally, any compound that meets the criterion of being a salt (consisting of an anion and cation) and is fluid at or near the reaction temperature or exists in a fluid state during any stage of the reaction may be defined as an ionic liquid.

The cation for the present process is preferably a 1,3-dialkylimidazolium cations. Other cations for this process are other substituted pyridinium or alkyl- or poly-alkylpyridinium, alkyl imidazolium, imidazole, alkyl or poly-alkylimidazolium, alkyl or polyalkylpyrazolium, ammonium, alkyl or polyalkyl ammonium, alkyl or poly-alkyl phosphonium cations.

The anion for the present process is preferably a nitrogen containing anion, such as nitrate, nitrite, alkylsulfate, or a chloride, bromide or other halide. Other anions include sulfur containing anions including sulfate or sulphite, hydrogensulfate, oxoanions of metals, selenium, tellurium, phosphorus, arsenic, antimony, and bismuth based anions.

More than one ionic liquid or any combination of ionic liquids may be used in the present invention.

Suitable Process Conditions

Temperature: ideally 20–100° C. but to include 0° C. to 250° C.

Pressure: ideally, atmospheric, but include 1 mbar to 100 Bar

Time: ideally 24–48 hours, can be 1 minute to 1 month.

In one embodiment the process uses neutral ionic liquids such as [emim] [$HSO_4$] and [emim] [$EtOSO_3$] as now shown

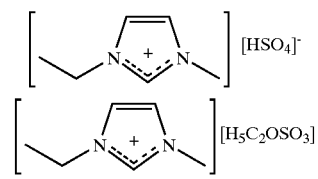

as media for the sulfonation reaction, and the use of sulfur trioxide alone as the sulfonating agent, as there would be no by-products from the reaction (as shown in the following reaction:

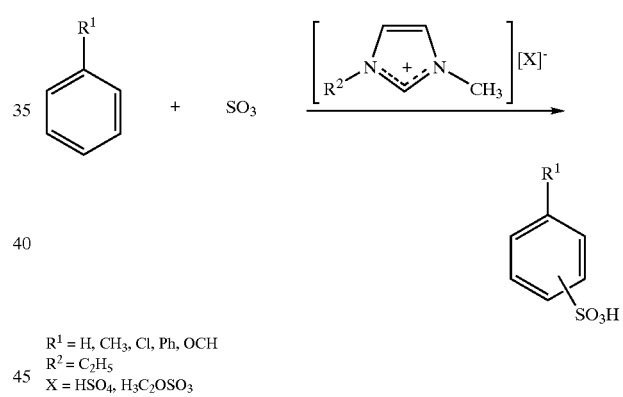

$R^1$ = H, $CH_3$, Cl, Ph, OCH
$R^2$ = $C_2H_5$
X = $HSO_4$, $H_3C_2OSO_3$

The sulfonation reactions of aromatic compounds using sulfur trioxide were found to be successful in two types of sulfate based ionic liquids. These were with ionic liquids containing the hydrogensulfate or ethylsulfate anion, and with a 1-ethyl-3-methylimidazolium cation. The results of the sulfonation of benzene and toluene are shown in Table 1.

TABLE 1

The sulfonation of aromatic compounds with $SO_3$, in ionic liquids.

| Aromatic Compound | Ionic Liquid | Eq.$SO_3$ | Temp./ ° C. | Time/ h. | Product(s) | % Yield |
|---|---|---|---|---|---|---|
| Benzene | [emim] [$HSO_4$] 0.5 eq | 0.42 | 80 | 18 | $C_6H_5$—$SO_3H$ | 99 |
| Benzene | [$C_{10}$mim] [OTf] | 1.1 | 25 | 1 | $C_6H_5$—$SO_3H$ | 99 |
| Toluene | [mim] [$HSO_4$] 3 eq | 0.25 | 25 | 8 | 2-$H_3C$—$C_6H_4$—$SO_3H$ 4-$H_3C$—$C_6H_4$—$SO_3H$ | 25 74 |

TABLE 1-continued

The sulfonation of aromatic compounds with SO$_3$, in ionic liquids.

| Aromatic Compound | Ionic Liquid | Eq.SO$_3$ | Temp./ ° C. | Time/ h. | Product(s) | % Yield |
|---|---|---|---|---|---|---|
| Toluene | [emim] [HSO$_4$] 3 eq | 0.25 | 80 | 30 | 2-H$_3$C—C$_6$H$_4$—SO$_3$H | 28 |
|  |  |  |  |  | 4-H$_3$C—C$_6$H$_4$—SO$_3$H | 71 |
| Toluene | [emim] [HSO$_4$] 0.8 eq | 0.25 | 80 | 5 | 2-H$_3$C—C$_6$H$_4$—SO$_3$H | 32 |
|  |  |  |  |  | 4-H$_3$C—C$_6$H$_4$—SO$_3$H | 67 |
| Toluene | [emim] [HSO$_4$] 0.8 eq | 0.25 | 80 | 30 | 2-H$_3$C—C$_6$H$_4$—SO$_3$H | 32 |
|  |  |  |  |  | 4-H$_3$C—C$_6$H$_4$—SO$_3$H | 67 |
| Toluene | [emim] [EtOSO$_4$] 0.75 eq | 0.25 | 80 | 5 | 2-H$_3$C—C$_6$H$_4$—SO$_3$H | 44 |
|  |  |  |  |  | 4-H$_3$C—C$_6$H$_4$—SO$_3$H | 55 |
| Toluene | [emim] [EtOSO$_4$] 0.75 eq | 0.25 | 80 | 18 | 2-H$_3$C—C$_6$H$_4$—SO$_3$H | 43 |
|  |  |  |  |  | 4-H$_3$C—C$_6$H$_4$—SO$_3$H | 56 |
| Toluene | [C$_{10}$mim] [OTf] 0.50 eq | 1.1 | 25 | 1 | 2-H$_3$C—C$_6$H$_4$—SO$_3$H | 22 |
|  |  |  |  |  | 2-H$_3$C—C$_6$H$_4$—SO$_3$H | 77 |

The sulfonation of benzene proceeds smoothly to give benzenesulfonic acid in almost quantitative yield, in the ionic liquid [emim] [HSO$_4$][11] as shown in scheme 2.

Scheme 2: Proposed Mechanism for the Sulfonation of Aromatic in Ionic Liquids

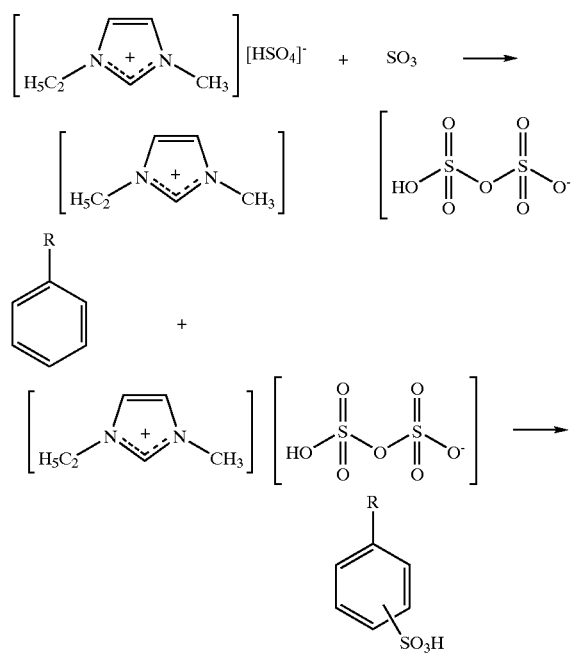

As can be seen, the sulfonation reaction proceeds to give the expected products with benzene and toluene (Table 1). Benzene is sulfonated to benzene sulfonic acid in 99% yield in [emim] [HSO$_4$] and [C$_{10}$mim] [OTf]. The sulfonation of toluene proceeded to give isomeric mixtures of toluene-sulfonic acids, as shown in Table 1. The best para to ortho isomer ratio was obtained in [C$_{10}$mim] [OTf] at 25° C. In several cases, the ionic liquids were found to function as a catalyst for the reaction, as the sulfur trioxide and arene were in excess over the ionic liquids used, and gave 98–99% yields.

The sulfonylation of toluene with chlorosulfuric acid in the ionic liquid [bmim] [NTf$_2$] was investigated and compared with a similar reaction in dichloromethane. See FIG. 1 and Table 2. The reaction in dichloromethane gave predominantly the sulfonyl chloride product, whereas in the ionic liquid, the sulfonic acid was the major product. In general, the o-, p-selectivities were higher in the ionic liquid, and for the formation of the sulfonyl chloride product.

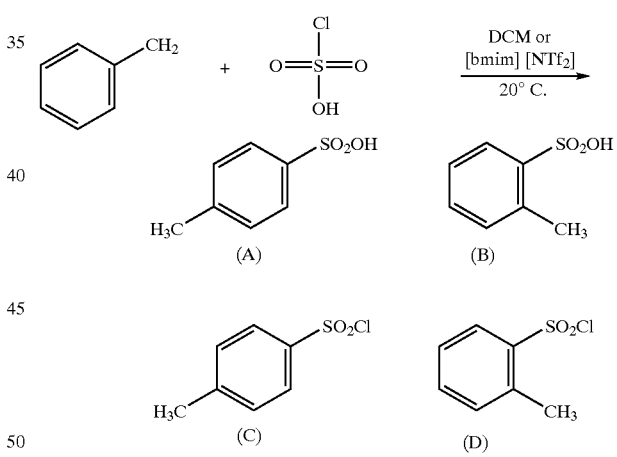

FIG. 1: The reaction of toluene with chlorosulfuric acid.

TABLE 2

The products and isomer ratios in the reaction of chlorosulfuric acid with toluene, in DCM and [bmim] [NTf$_2$] at 20° C.

| Solvent | % Yield (A) + (B) | (A/(B) | % Yield (C) + (D) | (C)/(D) |
|---|---|---|---|---|
| DCM | 15 | 1.4 | 85 | 1.8 |
| [bmim] [NTf$_2$] | 80 | 2.1 | 20 | 3.0 |

The reaction of 1,2,4-trichlorobenzene with chlorosulfuric acid gave rise to a 40 to 60 mixture of the corresponding chlorosulfonate and sulfonic acid at 150° C. in the ionic liquid [bmim] [NTf$_2$]. The chlorosulfonate intermediate sublimes out of the reaction vessel during the reaction. Addition of SO$_2$Cl$_2$ followed by heating at 150° C. for 24 hours resulted in the conversion of the sulfonic acid to the chlorosulfonate (FIG. 2). This reaction is the first step in the synthesis of the insecticide Tetradafion® (2,4,4',5-tetrachlorodiphenylsulfone). The yield in synthesis of the 2,4,5-trichlorochlorobenzenesulfonyl chloride was improves by using a 1:1 mixture of sulfuryl chloride and chlorosulfuric acid. This gave a 55% yield of the 2,4,5-trichlorochlorobenzenesulfonyl chloride.

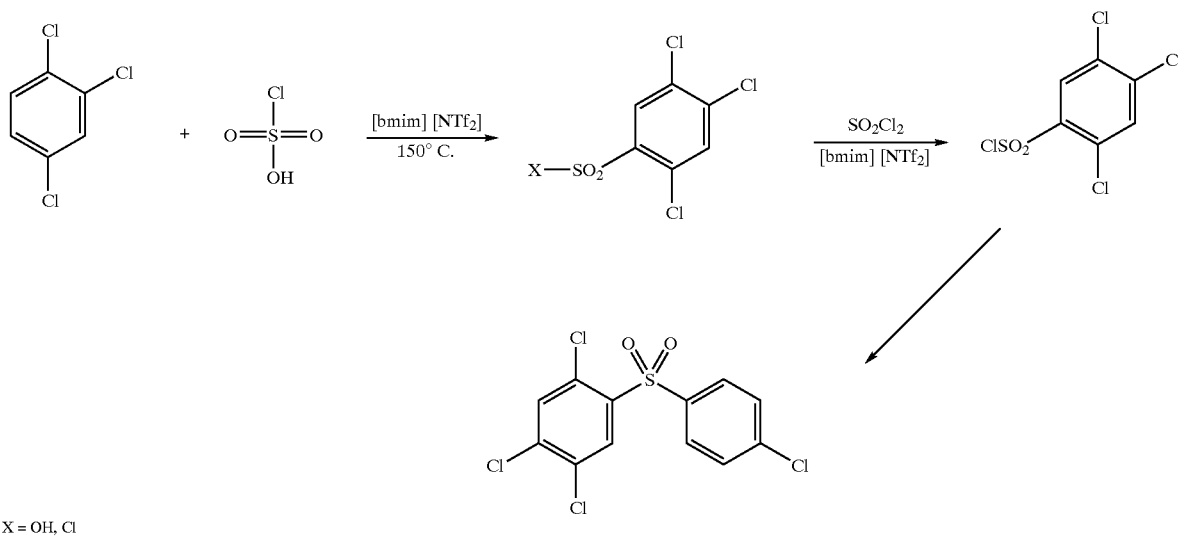

X = OH, Cl

FIG. 2: The sulfonation of trichlorobenzene.

The products of these reactions can be isolated in three separate ways. Vacuum distillation allows the products to be separated from this ionic liquid, which leaves the ionic liquid ready for reuse. However, this cannot be used for high molecular weight products because the high temperatures involved may decompose the product. Solvent extraction with ethyl acetate can be used to isolate the organic products from the reaction. The third and most successful approach is the use of steam distillation. Complete separation of the organic products from the ionic liquid can be achieved by the addition of water, followed by distillation at 140–160° C. at atmospheric pressure. The product can then be separated from the residual water usually by distillation and drying.

EXAMPLE 1

Sulfonation of Toluene in [C$_{10}$mim] [OTf]

In a round-bottomed flask (25 cm$^3$) equipped with a magnetic stirrer flea and stopper, 1-decyl-3-methylimidazolium trifluoromethanesulfonate (0.97 g, 2.5 mmol) and toluene (0.46g, 5.0 mmol) were added. Sulfur trioxide (0.44g, 5.5 mmol) was cautiously added (carried out in a dry box) and the mixture stirred for 1 hour. A crude sample was taken from the flask and analysed by NMR (CDCl$_3$, 300 MHz). This showed that the reaction was complete and gave 77% of p-toluenesulfonic acid and 22% o-toluenesulfonic acid. The products were isolated from the ionic liquid by Kugelrohr distillation at 1 mmHg. This gave colourless solid (bp=200° C. at 1 mmHg). The structures were confirmed by NMR analysis and were in accordance with authentic material.

EXAMPLE 2

(Chloro)sulfonation of Toluene

In a 50 cm$^3$ round bottomed flask, equipped with a magnetic stirrer and reflux condenser and ice bath, was added toluene (0.91g, 10 mmol) and [bmim] [NTf$_2$] (1.0 g). Chlorosulfuric acid (2.33g, 20 mmol) was cautiously added and the mixture stirred at 0° C. for 2 hours. The mixture was analysed by NMR and found to give >95% conversion to products. A similar reaction was performed using 1.0 g of dichloromethane in place of the [bmim] [NTf$_2$]. The product and isomer distributions for both reactions are given in Table 2.

EXAMPLE 3

(Chloro)sulfonation of 1,2,4-trichlorobenzene

In a 50 cm$^3$ round bottomed flask, equipped with a magnetic stirrer and reflux condenser, was added 1,2,4-trichlorobenzene (1.81 g, 10 mmol) and [bmim] [NTf$_2$] (1.0 g). Chlorosulfuric acid (2.33 g, 20 mmol) was cautiously added and the mixture heated at 150° C. After 24 hours the mixture was analysed by NMR and found to have given >99% conversion to products. The major products were identified as 2,4,5-trichlorochlorobenzenesulfonyl chloride (40%) and 2,4,5-trichlorochlorobenzenesulfonic acid (60%)

EXAMPLE 4

(Chloro)sulfonation of 1,2,4-trichlorobenzene

In a 50 cm$^3$ round bottomed flask, equipped with a magnetic stirrer and reflux condenser, was added 1,2,4-trichlorobenzene (4.21 g, 25 mmol) and [bmim] [NTf$_2$] (1.0 g). A mixture of chlorosulfuric acid (2.33 g, 20 mmol) and sulfuryl chloride (2.70 g, 20 mmol) was cautiously added and the mixture heated at 150° C. After 48 hours the mixture was analysed by NMR and found to give >95% conversion to products. The major products were identified as 2,4,5-trichlorochlorobenzenesulfonyl chloride (55%) and 2,4,5-trichlorochlorobenzenesulfonic acid (40%). The 2,4,5-trichlorochlorobenzenesulfonyl chloride was isolated by vacuum sublimation directly from the reaction vessel on a Kugelrohr apparatus and the 2,4,5-trichlorochlorobenzenesulfonic acid was isolate as its sodium salt, by reaction of the sublimation residue with an aqueous solution of sodium hydrogen carbonate. The ionic liquid (insoluble in this aqueous solution) was recovered.

In conclusion, sulfonation of aromatic compounds using sulfur trioxide or chlorosulfuric acid in ionic liquids proceeds efficiently to give the mono-sulfonated product. The ionic liquids could all be reused in further sulfonation reactions and were not destroyed in the reaction. Separation of the products was achieved by vacuum distillation, solvent extraction, or most notably, steam distillation. The reaction is clean, gives no by-products and is easy to perform.

The present invention also extends to the use of an ionic liquid in the sulfonation of aromatic compounds, as well as a sulfonated aromatic compound whenever prepared from a process of the present invention.

REFERENCES

[1] R. T. Morrison and R. N. Boyd "Organic Chemistry Second Edition", Allyn and Bacon Inc., Boston, 1969.
[2] H. R. W. Ansink, H. Cerfontain, H. *Journal of the Royal Netherlands Chemical Society*, 1992, 111, 183–187.
[3] T. M. Fatum, U. Anthoni, C. Christophersen, P. H. Nielsen, *Hetercycles*, 1994, 38, 1619–1625.
[4] O. Eiji, Y. Norio, K. Takayuki, U.S. Pat. No. 5,596,128, 1997.
[5] M. J. Earle and K. R. Seddon, *Pure and App. Chem.* 2000, in press.
[6] C. J. Adams, M. J. Earle, G. Roberts and K. R. Seddon. *Chem. Commun.* 1998, 2097–2098.
[7] C. J. Adams, M. J. Earle, J. Hamill, C. Lok, G. Roberts and K. R. Seddon, *World Patent WO* 98 07679, 1998.
[8] (a) B. Ellis, W. Keim and P. Wasserscheid, *Chem. Commun.* 1999, 337. (b) S. Einloft, H. Olivier and Y. Chauvin, U.S. Pat. No. 5,550,306, 1996.
[9] M. J. Earle, P. B. McCormac and K. R. Seddon, *Green Chem.* 1999, 123–25.
[10] (a) T. Fisher, A. Sethi, T. Welton, J. Woolf, *Tetrahedron Lett.* 1999, 40, 793–194. (b) C. J. Adams, M. J. Earle, K. R. Seddon, *Chem. Commun.* 1999, 1043–1044.
[11] Synthesised by heating [emim] [HSO$_4$] in water for 5 days, followed by drying under vacuum.

What is claimed is:

1. A process for the sulfonation of an aromatic compound comprising admixing the aromatic compound and a sulfonating agent in the presence of an ionic liquid consisting entirely of cations and anions.

2. The process as claimed in claim 1 wherein the cation of the ionic liquid is selected from the group consisting of 1,3-dialkylimidazolium, substituted pyridinium, alkyl pyridinium, polyalkylpyridinium, imidazole, alkyl imidazolium, polyalkylimidazolium, alkylpyrazolium, polyalkylpyrazolium, ammonium, alkyl ammonium, polyalkyl ammonium, alkyl phosphonium, poly-alkyl phosphonium, and combinations thereof.

3. The process as claimed in claim 2 wherein the cation is 1,3-dialkylimidazolium.

4. The process as claimed in claim 1 wherein the anion of the ionic liquid is selected from the group consisting of nitrogen-containing anions; alkylsulfate; halide; sulfur-containing anions; hydrogensulfate; oxoanions of metals; ions based on selenium, tellurium, phosphorus, arsenic, antimony, or bismuth; and combinations thereof.

5. The process as claimed in claim 4 wherein the anion is a nitrate, nitrite, alkylsulphate, chloride or bromide.

6. The process as claimed in claim 1 wherein more than one ionic liquid consisting entirely of cations and anions is present.

7. The process as claimed in claim 1 wherein the sulfonating agent is sulfur trioxide or chiorosulfuric acid.

8. The process as claimed in claim 1 wherein the ionic liquid is selected from the group consisting of [emim] [HSO$_4$], [emim] [EtOSO$_3$], [bmim] [NTf$_2$], [C$_{10}$mim] [OTf], and combinations thereof.

9. The process as claimed in claim 1 wherein the aromatic compound is benzene, trichlorobenzene or toluene.

10. The process as claimed in claim 1 wherein the reaction products are isolated by vacuum distillation, solvent extraction, or steam distillation, or a combination of two or more thereof.

11. The process as claimed in claim 1 for selective isomeric sulfonation of an aromatic compound.

12. The process as claimed in claim 1 providing mono-sulfonated product.

13. A sulfonated aromatic compound obtained by a process as defined in claim 1.

14. The compound as claimed in claim 13 being an arylsulfonic acid.

15. The compound as claimed in claim 14 being benzene, sulfonic acid or toluenesulfonic acid.

16. The compound as claimed in claim 14 being mono-substituted.

17. The process as claimed in claim 4 wherein the anion of the ionic liquid is a sulfate or suiphite.

18. The process as claimed in claim 10 wherein the solvent extraction is solvent extraction with a base.

19. The compound as claimed in claim 15 being mono-substituted.

* * * * *